(12) United States Patent
Schlaud et al.

(10) Patent No.: US 10,357,385 B2
(45) Date of Patent: Jul. 23, 2019

(54) LOW BLEED IMPLANTABLE PROSTHESIS WITH A TAPER

(71) Applicant: W. L. Gore & Associates, Inc., Newark, DE (US)

(72) Inventors: Marc A. Schlaud, Flagstaff, AZ (US); Timothy T. Stringer, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 188 days.

(21) Appl. No.: 15/173,361

(22) Filed: Jun. 3, 2016

(65) Prior Publication Data

US 2016/0354217 A1    Dec. 8, 2016

Related U.S. Application Data

(60) Provisional application No. 62/171,694, filed on Jun. 5, 2015.

(51) Int. Cl.
| | |
|---|---|
| *A61F 2/82* | (2013.01) |
| *A61F 2/06* | (2013.01) |
| *A61M 1/36* | (2006.01) |
| *A61L 31/04* | (2006.01) |
| *A61L 31/06* | (2006.01) |
| *A61L 31/10* | (2006.01) |

(52) U.S. Cl.
CPC .................. *A61F 2/82* (2013.01); *A61F 2/06* (2013.01); *A61L 31/048* (2013.01); *A61L 31/06* (2013.01); *A61L 31/10* (2013.01); *A61M 1/3655* (2013.01); *A61F 2210/0076* (2013.01); *A61F 2230/0069* (2013.01); *A61F 2250/0036* (2013.01); *A61F 2250/0039* (2013.01); *A61L 2420/08* (2013.01)

(58) Field of Classification Search
CPC ...... A61F 2/82; A61F 2/06; A61F 2/00; A61F 2210/0076; A61F 2230/0069; A61F 2250/00397; A61L 31/048; A61L 31/06; A61L 31/10; A61L 2420/08; A61M 1/3655

See application file for complete search history.

(56) References Cited

U.S. PATENT DOCUMENTS

| | | |
|---|---|---|
| 512,151 A | 1/1894 | Briggs |
| 3,425,418 A | 2/1969 | Chvapil et al. |

(Continued)

FOREIGN PATENT DOCUMENTS

| | | |
|---|---|---|
| CN | 1466165 A | 1/2004 |
| EP | 0117072 | 8/1984 |

(Continued)

OTHER PUBLICATIONS

International Search Report and Written Opinion for PCT/US2014/068411 dated Feb. 12, 2015, corresponding to U.S. Appl. No. 14/557,927, 9 pages.

(Continued)

*Primary Examiner* — Philip R Wiest (57) ABSTRACT

A vascular graft having a sealing layer and a tapered length portion. The sealing layer provides the vascular graft with low bleed characteristics subsequent to a needle puncture such as with a dialysis needle or a suture needle. The sealing layer in the tapered length portion has varying wall thickness along the tapered length portion.

20 Claims, 7 Drawing Sheets

(56) References Cited

U.S. PATENT DOCUMENTS

| | | |
|---|---|---|
| 3,814,137 A | 6/1974 | Martinez |
| 3,914,802 A | 10/1975 | Reick |
| 3,953,566 A | 4/1976 | Gore |
| 4,133,927 A | 1/1979 | Tomodoa et al. |
| 4,177,334 A | 12/1979 | Okita |
| 4,187,390 A | 2/1980 | Gore |
| 4,193,138 A | 3/1980 | Okita |
| 4,208,745 A | 6/1980 | Okita |
| 4,229,838 A | 10/1980 | Sumitomo |
| 4,279,245 A | 7/1981 | Takagi et al. |
| 4,283,448 A | 8/1981 | Bowman |
| 4,304,010 A | 12/1981 | Mano |
| 4,321,711 A | 3/1982 | Mano |
| 4,347,204 A | 8/1982 | Takagi et al. |
| 4,416,028 A | 11/1983 | Eriksson et al. |
| 4,443,511 A | 4/1984 | Worden et al. |
| 4,474,630 A | 10/1984 | Planck et al. |
| 4,478,898 A | 10/1984 | Kato |
| 4,550,447 A | 11/1985 | Seiler, Jr. et al. |
| 4,604,762 A | 8/1986 | Robinson |
| 4,613,544 A | 9/1986 | Burleigh |
| 4,619,641 A | 10/1986 | Schanzer |
| 4,657,544 A | 4/1987 | Pinchuk |
| 4,687,482 A | 8/1987 | Hanson |
| 4,692,369 A | 9/1987 | Nomi |
| 4,731,073 A | 3/1988 | Robinson |
| 4,739,013 A | 4/1988 | Pinchuk |
| 4,743,252 A | 5/1988 | Martin, Jr. et al. |
| 4,743,480 A | 5/1988 | Campbell et al. |
| 4,759,757 A | 7/1988 | Pinchuk |
| 4,787,921 A | 11/1988 | Shibata et al. |
| 4,804,381 A | 2/1989 | Turina et al. |
| 4,810,749 A | 3/1989 | Pinchuk |
| 4,816,339 A | 3/1989 | Tu |
| 4,850,999 A | 7/1989 | Planck |
| 4,857,069 A | 8/1989 | Kira |
| 4,871,361 A | 10/1989 | Kira |
| 4,875,468 A | 10/1989 | Krauter et al. |
| 4,877,661 A | 10/1989 | House et al. |
| 4,882,113 A | 11/1989 | Tu et al. |
| 4,891,407 A | 1/1990 | Mitchell |
| 4,921,495 A | 5/1990 | Kira |
| 4,932,964 A | 6/1990 | Bittmann et al. |
| 4,945,125 A | 7/1990 | Dillon et al. |
| 4,955,899 A | 9/1990 | Della Coma et al. |
| 4,957,669 A | 9/1990 | Primm |
| 4,969,896 A | 11/1990 | Shors |
| 4,973,609 A | 11/1990 | Browne |
| 5,024,671 A | 6/1991 | Tu et al. |
| 5,026,513 A | 6/1991 | House |
| 5,061,276 A | 10/1991 | Tu et al. |
| 5,064,593 A | 11/1991 | Tamaru et al. |
| 5,066,683 A | 11/1991 | Dillon et al. |
| 5,071,609 A | 12/1991 | Tu et al. |
| 5,084,065 A | 1/1992 | Weldon et al. |
| 5,100,422 A | 3/1992 | Berguer et al. |
| 5,104,400 A | 4/1992 | Berguer et al. |
| 5,116,360 A | 5/1992 | Pinchuk et al. |
| 5,123,917 A | 6/1992 | Lee |
| 5,128,092 A | 7/1992 | Asaumi et al. |
| 5,133,742 A | 7/1992 | Pinchuk |
| 5,152,782 A | 10/1992 | Kowligi et al. |
| 5,192,310 A | 3/1993 | Herweck et al. |
| 5,217,797 A | 6/1993 | Knox et al. |
| 5,229,431 A | 7/1993 | Pinchuk |
| 5,290,271 A | 3/1994 | Jernberg |
| 5,320,888 A | 6/1994 | Stevens |
| 5,354,329 A | 10/1994 | Whalen |
| 5,358,516 A | 10/1994 | Myers et al. |
| 5,370,681 A | 12/1994 | Herweck et al. |
| 5,453,235 A | 9/1995 | Calcote et al. |
| 5,466,252 A | 11/1995 | Soukup et al. |
| 5,476,589 A | 12/1995 | Bacino |
| 5,584,876 A | 5/1996 | Bruchman et al. |
| 5,527,353 A | 6/1996 | Schmitt |
| 5,529,820 A | 6/1996 | Nomi et al. |
| 5,549,664 A | 8/1996 | Hirata et al. |
| 5,556,426 A | 9/1996 | Popadiuk et al. |
| 5,607,478 A | 3/1997 | Lentz et al. |
| 5,609,624 A | 3/1997 | Kalis |
| 5,620,763 A | 4/1997 | House et al. |
| 5,628,782 A | 5/1997 | Myers et al. |
| 5,628,788 A | 5/1997 | Pinchuk |
| 5,641,373 A | 6/1997 | Shannon et al. |
| 5,647,400 A | 7/1997 | Jani et al. |
| 5,665,114 A | 9/1997 | Weadock et al. |
| 5,700,287 A | 12/1997 | Myers et al. |
| 5,708,044 A | 1/1998 | Branca |
| 5,716,395 A | 2/1998 | Myers et al. |
| 5,716,660 A | 2/1998 | Weadock et al. |
| 5,718,973 A | 2/1998 | Lewis et al. |
| 5,735,892 A | 4/1998 | Myers et al. |
| 5,749,880 A | 5/1998 | Banas et al. |
| 5,788,626 A | 8/1998 | Thompson |
| 5,789,047 A | 8/1998 | Sasaki et al. |
| 5,800,510 A | 9/1998 | Schmitt |
| 5,800,512 A | 9/1998 | Lentz et al. |
| 5,800,514 A | 9/1998 | Nunez |
| 5,824,050 A | 10/1998 | Karwoski et al. |
| 5,840,240 A | 11/1998 | Stenoien |
| 5,843,173 A | 12/1998 | Shannon et al. |
| 5,851,229 A | 12/1998 | Lentz et al. |
| 5,851,230 A | 12/1998 | Lentz et al. |
| 5,866,217 A | 2/1999 | Stenoien et al. |
| 5,897,587 A | 4/1999 | Martakos et al. |
| 5,904,967 A | 5/1999 | Ezaki et al. |
| 5,910,168 A | 6/1999 | Myers et al. |
| 5,931,865 A | 8/1999 | Silverman et al. |
| 5,976,192 A | 11/1999 | McIntyre et al. |
| 6,001,125 A | 12/1999 | Golds et al. |
| 6,016,848 A | 1/2000 | Egres et al. |
| 6,027,779 A | 2/2000 | Campbell et al. |
| 6,036,724 A | 3/2000 | Lentz et al. |
| 6,039,755 A | 3/2000 | Edwin |
| 6,042,666 A | 3/2000 | Karwoski et al. |
| 6,053,939 A | 4/2000 | Okuda et al. |
| 6,056,970 A | 5/2000 | Greenawalt et al. |
| 6,080,198 A | 6/2000 | Lentz et al. |
| 6,099,557 A | 8/2000 | Schmitt |
| 6,159,565 A | 12/2000 | Campbell et al. |
| 6,165,211 A | 12/2000 | Thompson |
| 6,187,054 B1 | 2/2001 | Colone et al. |
| 6,203,735 B1 | 3/2001 | Edwin |
| 6,267,834 B1 | 7/2001 | Shannon et al. |
| 6,287,337 B1 | 9/2001 | Martakos et al. |
| 6,319,279 B1 | 11/2001 | Shannon et al. |
| 6,328,762 B1 | 12/2001 | Anderson et al. |
| 6,338,904 B1 | 1/2002 | Patnaik et al. |
| 6,346,273 B1 | 2/2002 | Saettone |
| 6,368,347 B1 | 4/2002 | Maini et al. |
| 6,416,537 B1 | 7/2002 | Martakos et al. |
| 6,428,571 B1 | 8/2002 | Lentz et al. |
| 6,436,135 B1 | 8/2002 | Goldfarb |
| 6,517,571 B1 | 2/2003 | Brauker |
| 6,517,858 B1 | 2/2003 | LeMoel et al. |
| 6,521,284 B1 | 2/2003 | Parsons et al. |
| 6,534,084 B1 | 3/2003 | Vyakarnam et al. |
| 6,541,589 B1 | 4/2003 | Baillie |
| 6,547,820 B1 | 4/2003 | Staudenmeier |
| 6,589,468 B1 | 7/2003 | Schmitt |
| 6,663,614 B1* | 12/2003 | Carter .............. A61M 25/0009 604/264 |
| 6,712,919 B2 | 3/2004 | Ruefter et al. |
| 6,716,239 B2 | 4/2004 | Sowinski |
| 6,719,783 B2 | 4/2004 | Lentz et al. |
| 6,790,226 B2 | 9/2004 | Edwin et al. |
| 6,814,753 B2 | 11/2004 | Schmitt |
| 6,827,737 B2 | 12/2004 | Hill et al. |
| 6,863,686 B2 | 3/2005 | Shannon et al. |
| 6,926,735 B2 | 8/2005 | Henderson |
| 6,939,377 B2 | 9/2005 | Jayaraman et al. |
| 7,056,336 B2 | 6/2006 | Armstrong et al. |
| 7,056,387 B2 | 6/2006 | Van Der Steur |
| 7,108,701 B2 | 9/2006 | Evens et al. |

(56) References Cited

U.S. PATENT DOCUMENTS

| | | |
|---|---|---|
| 7,147,617 B2 | 12/2006 | Henderson et al. |
| 7,244,271 B2 | 7/2007 | Lentz et al. |
| 7,297,158 B2 | 11/2007 | Jensen |
| 7,306,729 B2 | 12/2007 | Bacino et al. |
| 7,351,257 B2 | 4/2008 | Kaldany |
| 7,396,363 B2 | 7/2008 | Frid |
| 7,452,374 B2 | 11/2008 | Hain et al. |
| 7,510,571 B2 | 3/2009 | Spiridigliozzi et al. |
| 7,531,611 B2 | 5/2009 | Sabol et al. |
| 7,553,326 B2 | 6/2009 | Sweet et al. |
| 7,560,006 B2 | 7/2009 | Rakos et al. |
| 8,029,563 B2 | 10/2011 | House |
| 8,637,144 B2 | 1/2014 | Ford |
| 8,906,087 B2 | 12/2014 | House |
| 9,139,669 B2 | 9/2015 | Xu et al. |
| 2002/0058991 A1 | 5/2002 | Schmitt |
| 2002/0138129 A1 | 9/2002 | Armstrong et al. |
| 2003/0004559 A1 | 1/2003 | Lentz et al. |
| 2003/0027775 A1 | 2/2003 | Wallace |
| 2003/0060871 A1 | 3/2003 | Hill et al. |
| 2003/0100859 A1 | 5/2003 | Henderson et al. |
| 2003/0139806 A1 | 7/2003 | Haverkost et al. |
| 2003/0153983 A1 | 8/2003 | Miller et al. |
| 2004/0024442 A1 | 2/2004 | Sowinski et al. |
| 2004/0033364 A1 | 2/2004 | Spiridigliozzi et al. |
| 2004/0049264 A1 | 3/2004 | Sowinski et al. |
| 2004/0054406 A1 | 3/2004 | Dubson et al. |
| 2004/0122507 A1 | 6/2004 | Henderson |
| 2004/0182511 A1 | 9/2004 | Rakos et al. |
| 2004/0193242 A1 | 9/2004 | Lentz et al. |
| 2004/0215337 A1* | 10/2004 | Hain .................. A61F 2/07 623/1.44 |
| 2004/0265352 A1 | 12/2004 | Kaldany |
| 2005/0137677 A1 | 6/2005 | Rush |
| 2005/0187607 A1 | 8/2005 | Akhtar et al. |
| 2005/0240261 A1 | 10/2005 | Rakos |
| 2005/0249776 A1 | 11/2005 | Chen et al. |
| 2006/0041318 A1 | 2/2006 | Shannon |
| 2007/0116736 A1 | 5/2007 | Argentieri et al. |
| 2007/0276474 A1 | 11/2007 | Llanos et al. |
| 2007/0293808 A1 | 12/2007 | Williams et al. |
| 2008/0027534 A1 | 1/2008 | Edwin et al. |
| 2008/0097592 A1* | 4/2008 | Fitzpatrick ........... A61F 2/06 623/1.49 |
| 2008/0195026 A1 | 8/2008 | Kim |
| 2008/0195079 A1 | 8/2008 | Moore et al. |
| 2009/0270973 A1 | 10/2009 | Chen et al. |
| 2011/0054586 A1 | 3/2011 | Mayberry et al. |
| 2012/0130477 A1 | 5/2012 | Gessaroli |
| 2015/0157444 A1 | 6/2015 | Cully et al. |

FOREIGN PATENT DOCUMENTS

| | | |
|---|---|---|
| EP | 0256748 | 2/1988 |
| EP | 0266035 | 5/1988 |
| EP | 0391586 A2 | 10/1990 |
| EP | 656196 A1 | 7/1995 |
| EP | 1131113 B1 | 2/2000 |
| EP | 1101458 | 5/2001 |
| EP | 1925270 | 5/2008 |
| GB | 2033232 | 5/1980 |
| GB | 1590101 | 5/1981 |
| GB | 2222954 | 3/1990 |
| JP | 6343688 | 12/1994 |
| JP | 2739420 | 3/1995 |
| JP | 8238263 | 9/1996 |
| JP | 11099163 | 4/1999 |
| JP | 5176947 | 7/2010 |
| JP | 5474514 | 6/2011 |
| JP | 5925725 | 11/2014 |
| WO | WO-1995010247 | 4/1995 |
| WO | WO-1996007370 A1 | 3/1996 |
| WO | WO-9826731 | 6/1998 |
| WO | WO-2001021107 | 3/2001 |
| WO | WO-2001032382 | 5/2001 |
| WO | WO-2001067991 | 9/2001 |
| WO | WO-2002013675 A2 | 2/2002 |
| WO | WO-03015837 | 2/2003 |
| WO | WO-2003084440 | 10/2003 |
| WO | WO-2004060209 | 7/2004 |
| WO | WO-2004096307 | 11/2004 |
| WO | WO-2006/007214 | 1/2006 |
| WO | WO-2006026725 | 3/2006 |
| WO | WO-2006038031 | 4/2006 |
| WO | WO-2006085044 A1 | 8/2006 |
| WO | WO-2007061787 | 5/2007 |
| WO | WO-2007113494 | 10/2007 |
| WO | WO-2007127802 | 11/2007 |
| WO | WO-2007137211 | 11/2007 |

OTHER PUBLICATIONS

International Search Report and Written Opinion for PCT/US2016/035857 dated Aug. 4, 2016, corresponding to U.S. Appl. No. 15/173,361, 11 pages.

Berman M, Pearce W, et al, The use of Gore-Tex E-PTFE bonded to silicone rubber as an alloplastic implant material. Laryngoscope 1986; v96 n5: 480-483.

GORE® Acuseal Cardiovascular Patch Product Information, Jun. 2014, 40 pages.

International Search Report and Written Opinion for PCT/US2016/035857 dated Aug. 4, 2016, corresponding to U.S. Appl. No. 15/173,361, 9 pages.

LeMatire Expedial Vascular Access Graft Product Information/Instructions for Use.

Lumsden AB, Chen C et al. Nonporous silicone polymer coating of expanded polytetrafluoroethylene grafts reduces graft neointimal hyperplasia in dog and baboon models. Journal of Vascular Surgery 1996; v24 n5: 825-833.

Perma-Seal Dialysis Access Graft Instructions for use.

Perma-Seal Dialysis Access Graft Patient Education Brochure.

Sonoda H, Takamizawa K et al. Coaxial double-tubular compliant arterial graft prosthesis: time-dependent morphogenesis and compliance changes after implantation. J Biomed Mater Res 2003; 65A: 170-181.

Sonoda H, Takamizawa K et al. Small-diameter compliant arterial graft prosthesis: Design concept of coaxial double tubular graft and its fabrication. J Biomed Mater Res 2011; 55: 266-276.

European Search Report from EP18208417.8, dated Apr. 24, 2019, 8 pages.

* cited by examiner

LOW BLEED IMPLANTABLE PROSTHESIS WITH A TAPER

FIELD

The present disclosure relates to implantable devices such as vascular grafts, and more particularly, relates to low bleed tubular vascular grafts with a tapered length portions such that opposing ends of the graft have different inside diameters.

BACKGROUND

The use of implantable medical devices in the treatment of diseased vasculature and other body conduits has become commonplace in the medical field. These implantable devices can be used in applications where a low bleed implantable device is desired wherein the implantable device may be punctured (e.g., by suture needles and/or dialysis needles) and upon subsequent removal of the puncturing needle there is minimal fluid loss at the needle puncture site. Some of these implantable medical devices (e.g., a graft) may also be used in applications (e.g., dialysis) where a graft may benefit from a taper portion along its length, whereby one end of the graft has a larger inside diameter than an opposing end. A typical graft that has been designed for needle puncture may include an elastomeric material (e.g., silicone) that has a consistent wall thickness along the length of the graft. A typical graft, for example, a porous expanded polytetrafluoroethylene (ePTFE) graft that has been manufactured with a taper has a wall thickness at large end of the taper that is less than a wall thickness at a small end of the taper, therefore potentially limiting flexibility.

These tapered grafts and low bleed grafts have functioned well in many applications, particularly for dialysis applications. These previously known grafts still have limitations and leave room for improvements, especially in difficult applications such as where a low bleed graft and a taper is desired. Therefore, it remains desirable to provide a low bleed taper graft that has desirable handling attributes. There remains a need among vascular surgeons for such a graft.

SUMMARY

This document describes an implantable medical device, such as a vascular graft, incorporating a taper length portion and having low bleed characteristics following puncture by and removal of a needle such as a dialysis needle or a suture needle. A vascular graft per this disclosure may comprise a tubular structure having a first (Inner) layer, an intermediate layer, an optional second (outer) layer, and a length wherein said intermediate layer comprises an elastomer; wherein said tubular structure has a proximal end with proximal inside and outside diameters, and a distal end with a distal inside and outside diameters, wherein the distal inner and outer diameters are greater than the proximal inside and outside diameters respectively, and there is a transition length portion located between the proximal diameters and the distal diameters; and wherein the intermediate layer has a variable thickness along the length of the tubular structure and particularly along the transition length portion, wherein the thickness of the intermediate layer is greater at the distal end than it is at the proximal end. The first inner layer and the second outer layer may, in contrast to the intermediate layer (and counterintuitively), also be of variable thickness along the transition length portion but vary from being thicker at the proximal end to thinner at the distal end.

It is apparent that additional layers of materials as desired may be added to the three layer constructs described herein, resulting in constructs having four, five, six or more layers. In one embodiment, a first, inner layer may be a porous (e.g., ePTFE) material, an intermediate layer may be a non-porous (e.g., an elastomer) material, and an optional second, outer layer may be a porous (e.g., ePTFE) material. All materials should be suitable implantable materials. Suitable porous materials in addition to ePTFE may, for example, include implantable fabrics (e.g., polyethylene terephthalate) and porous polyurethanes and polyethylenes. Intermediate layer materials may include elastomers such as silicones and polyurethanes. These intermediate layer materials would most typically be non-porous materials, but porous versions of these same materials may also be used for this layer.

As layers extend along proximal, transition, and distal length portions; the materials making up the various layers may extend continuously and integrally between opposing ends of the graft. Alternatively, the various layers may be discreet, resulting in material boundaries between various length portions.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

DETAILED DESCRIPTION

Figure 1:
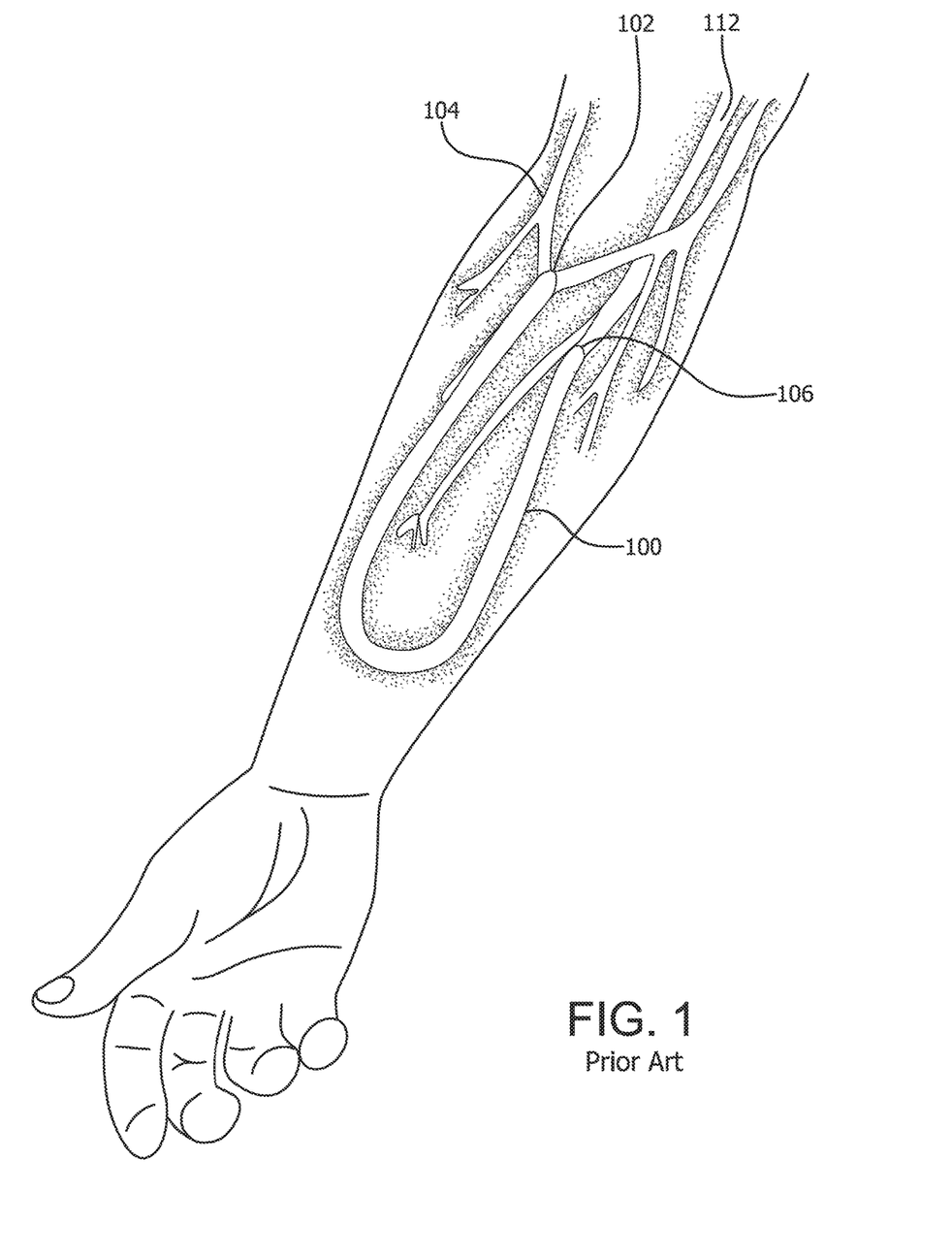
FIG. 1 shows an isometric view of human anatomy with an implantable device.

An implantable device (e.g., a vascular graft) in accordance with the present disclosure may be used in various applications. The implantable device 100 may be used in an arterial venous application (e.g., dialysis) as shown by example in FIG. 1. The implantable device (e.g., graft) 100 may have a distal end 102 that may be in communication with venous vasculature 104 and a proximal end 106 that may be in communication with arterial vasculature 112 and a length between the proximal end and the distal end. The graft may have a tubular shape along the length of the graft. The implantable device 100 could also be a stent-graft or a hybrid of a stent-graft and a vascular graft.

Figure 2:
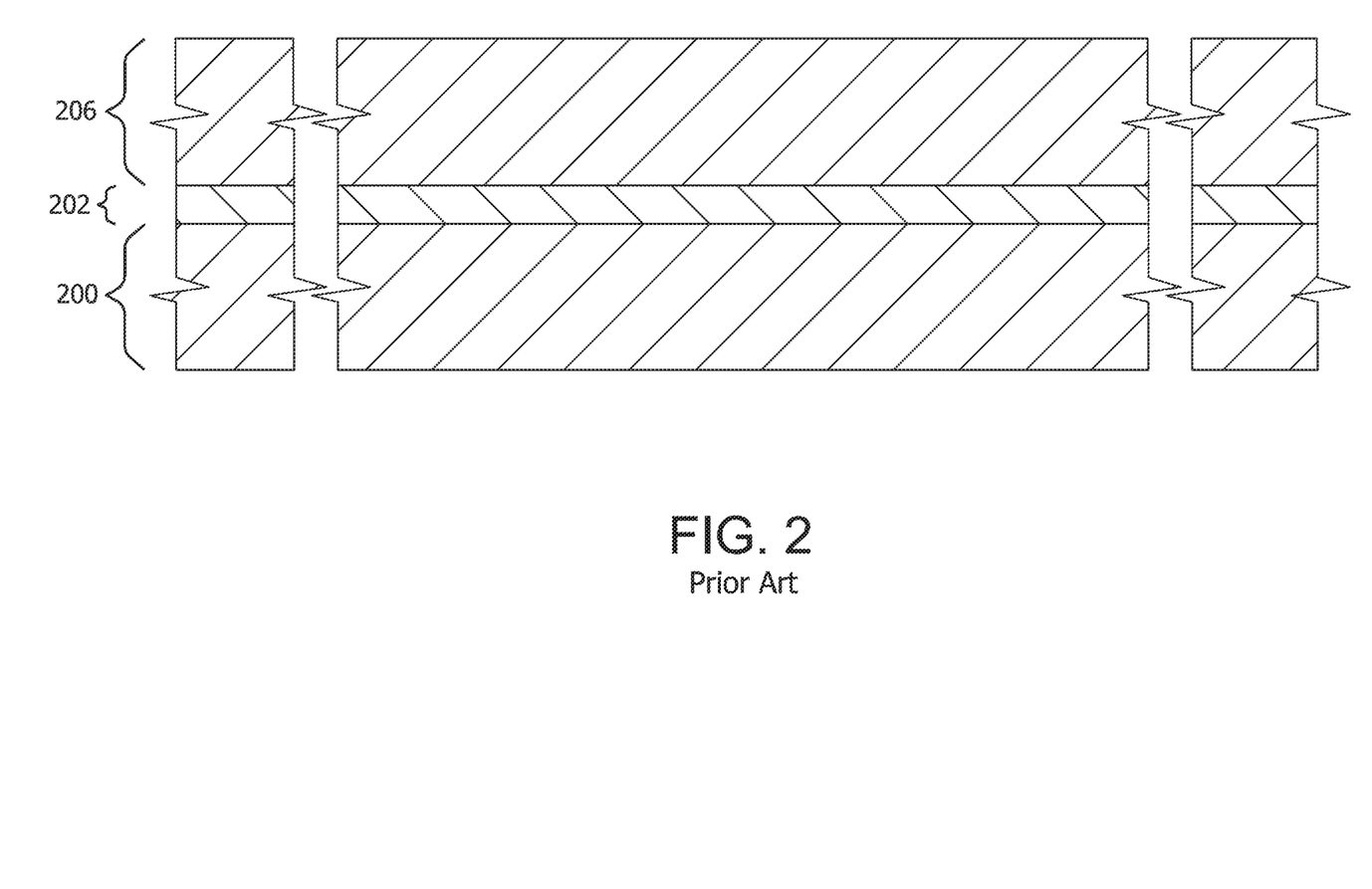
FIGS. 2 shows a longitudinal cross section of a previously known implantable device with low bleed characteristics.

FIG. 2 shows a longitudinal cross section of a portion of a length of previously known vascular graft with a first (inner) layer 200, an intermediate layer 202, and a second (outer) layer 206. The intermediate layer 202 (which may, for example, be an elastomer layer) is shown to have a constant wall thickness along the length of the vascular graft.

Figure 3A:
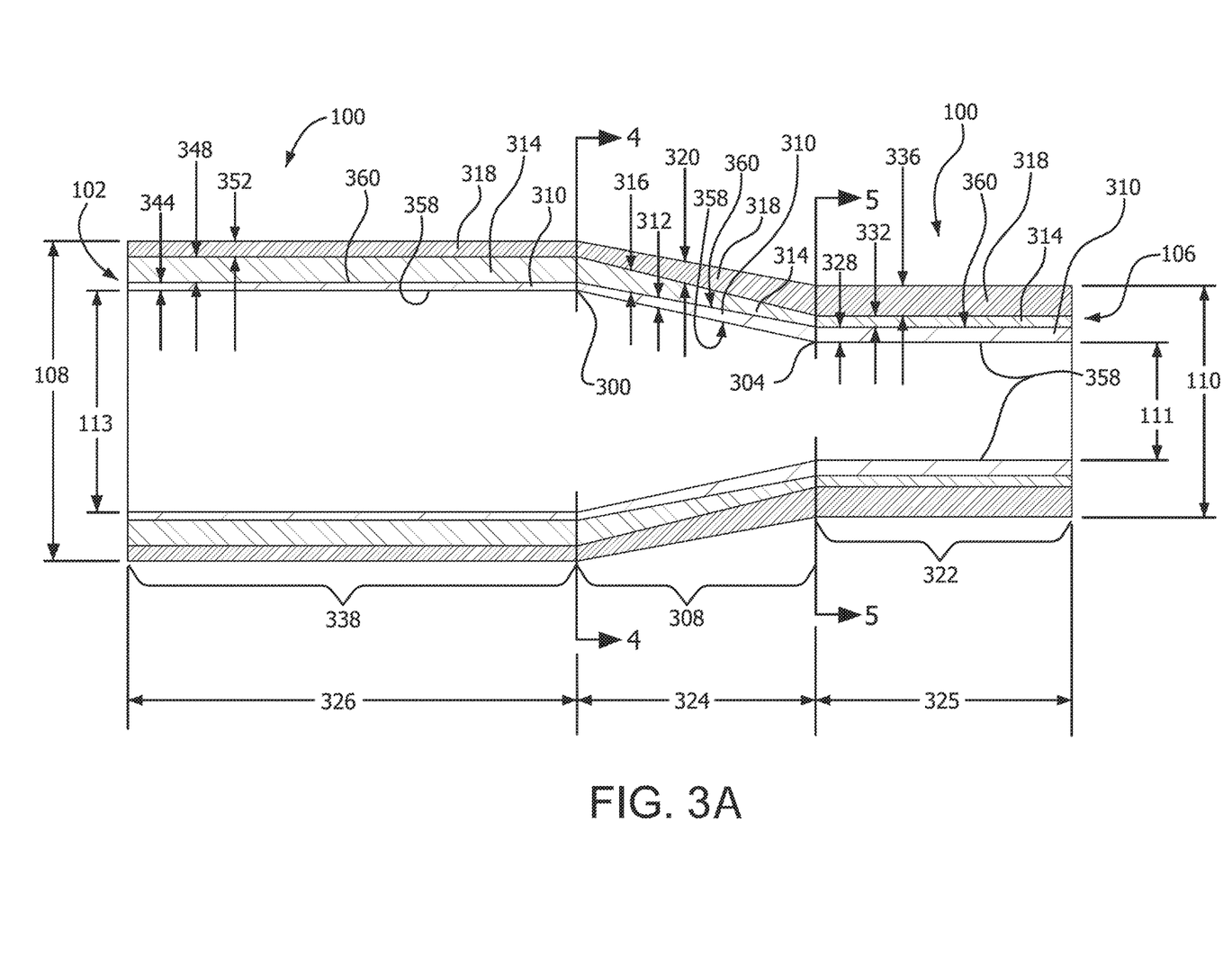
FIG. 3A shows a longitudinal cross section side view of an implantable device in accordance with the present disclosure.
Figure 3B:
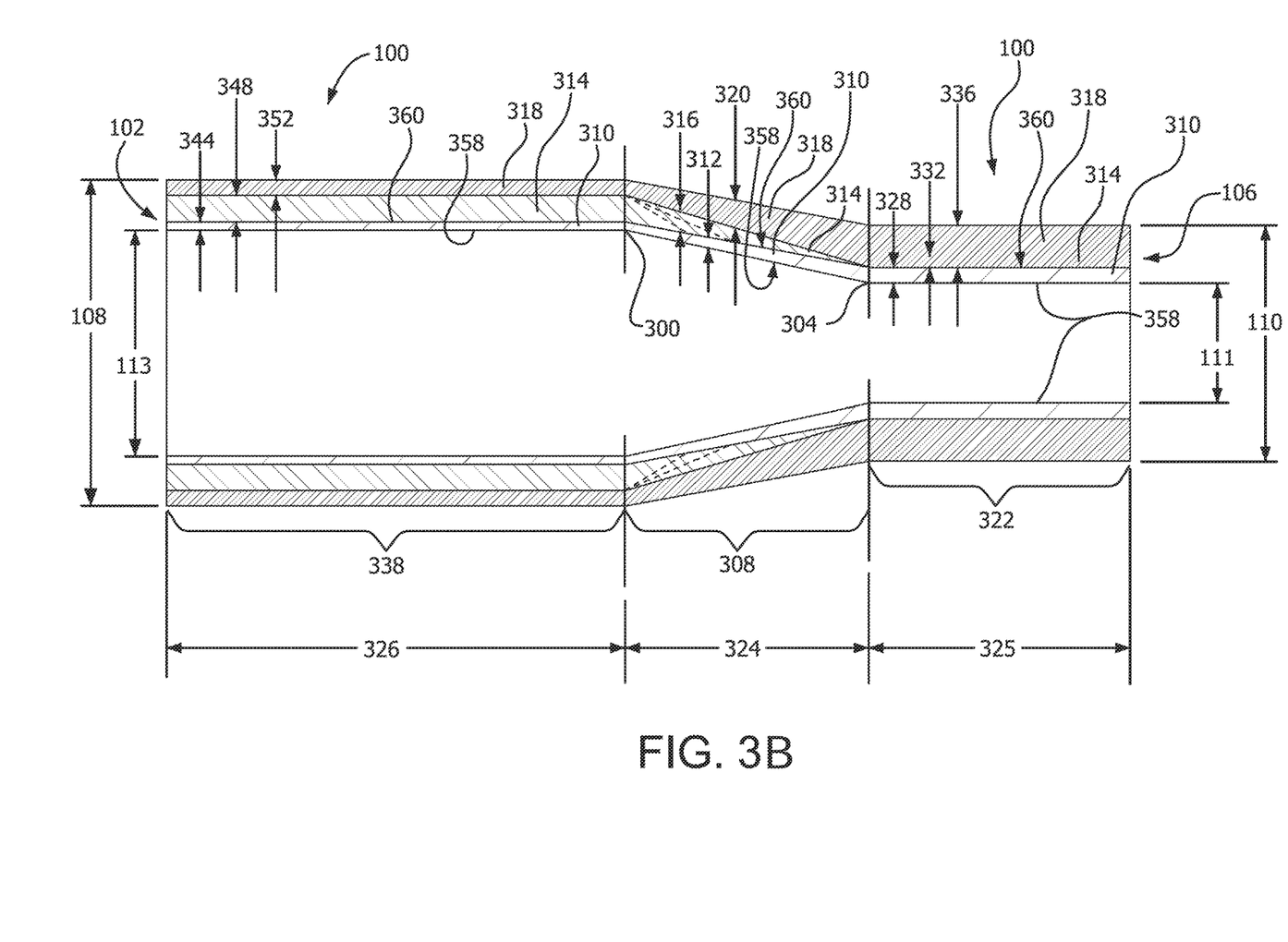
FIG. 3B shows a longitudinal cross section side view of an implantable device in accordance with the present disclosure.
Figure 3C:
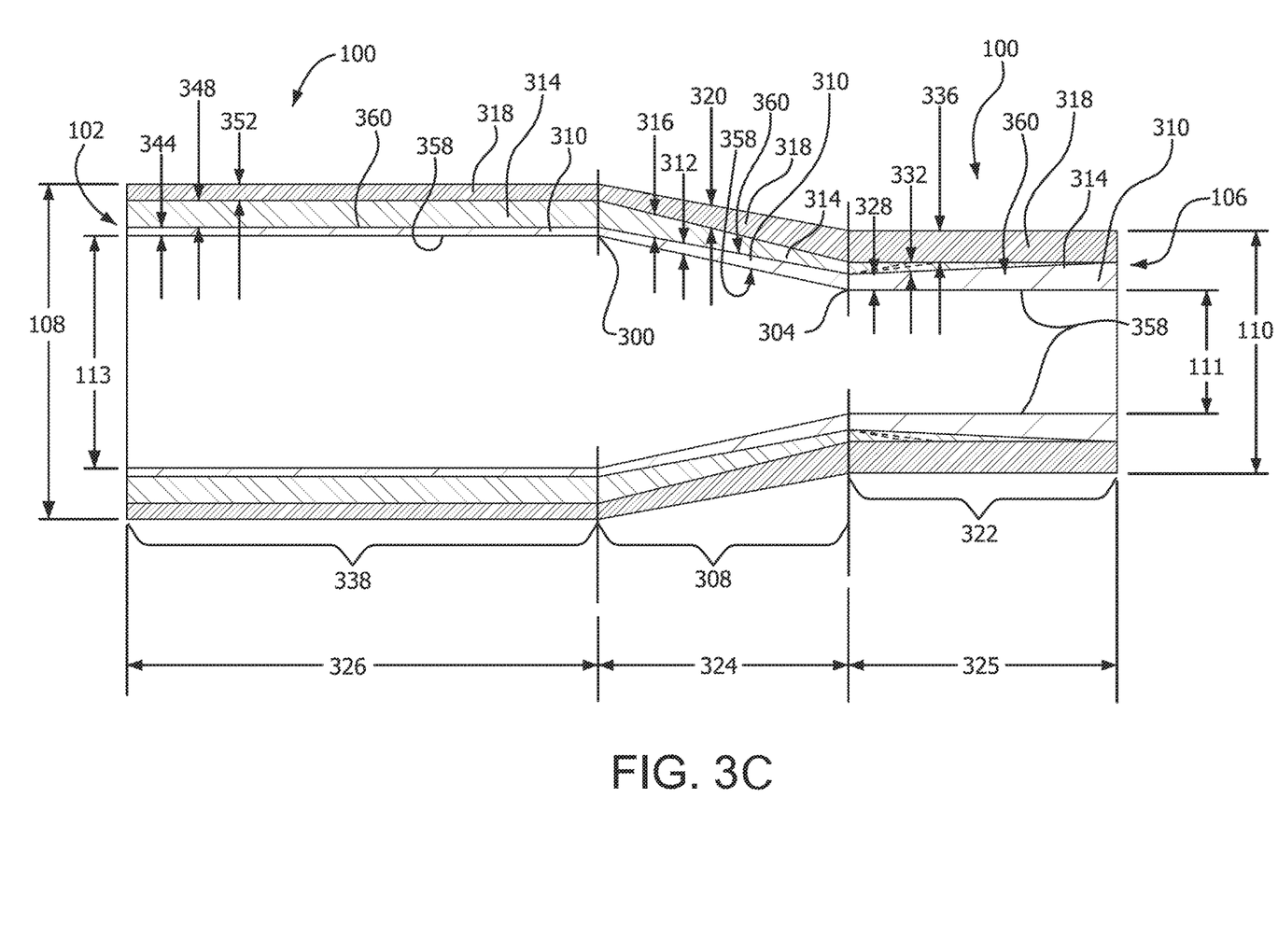
FIG. 3C shows a longitudinal cross section side view of an implantable device in accordance with the present disclosure.

An implantable device 100 can have various configurations. For example, as shown in the longitudinal cross section of FIGS. 3A-C and the transverse cross sections of FIG. 4 and FIG. 5, the implantable device 100 (e.g., a low bleed vascular graft) has a distal portion distal end 102 with a distal portion outer diameter 108 and a distal portion inside diameter 113. The implantable device 100, as shown in FIGS. 3A-C, has a proximal portion proximal end 106 with a proximal portion outer diameter 110 that is smaller than distal portion outer diameter 108 and a proximal portion inside diameter 111 that is smaller than the distal portion inside diameter 113. Located between the proximal portion proximal end 106 and the distal portion distal end 102, the implantable device 100 may have a proximal portion 322, a tapered transition portion 308, and a distal portion 338. In one application, for example, in a dialysis application, the proximal portion proximal end 106 may be in communication with an artery and the distal portion distal end 102 may be in communication with a vein. Alternatively, the proximal portion proximal end 106 may be in communication with a vein and the distal portion distal end 102 may be in communication with an artery. In other examples, the implantable device 100 may consist entirely of a transition portion 308, meaning the implantable device 100 is tapered entirely along its length between the proximal end 106 and the distal end 102.

The transition portion 308 has a transition portion length 324 between a transition portion proximal end 304 and transition portion distal end 300. The transition portion 308 may comprise a first (inner) layer 310 having a transition portion first layer wall thickness 312. The transition portion first layer wall thickness 312 may vary along the transition portion length 324. The transition portion first layer wall thickness 312 may be thicker on the transition portion proximal end 304 than the transition portion first layer wall thickness 312 at the transition portion distal end 300. Alternatively, the transition portion first layer wall thickness 312 may be thinner on the transition portion proximal end 304 than the transition portion first layer wall thickness 312 at the transition portion distal end 300.

The first layer 310 has a first layer first surface 358 and a first layer second surface 360, as shown in FIGS. 3A-C. The first layer first surface 358 and the first layer second surface 360 may extend along the implantable device 100 (e.g., along the proximal portion 322, transition portion 308, and the distal portion 338 or a combination thereof). As shown by example in FIGS. 3A-C, the first layer first surface 358 and the first layer second surface 360 extend along the proximal portion 322, transition portion 308, and the distal portion 338.

The transition portion 308 may also have an intermediate layer 314 adjacent to at least a portion of the first layer 310. For example, as shown in FIGS. 3A-C, the transition portion 308 has an intermediate layer 314 adjacent to or juxtaposed to the first layer second surface 360. Alternatively, the intermediate layer 314 may be partially imbibed into porous first layer 310 near the interface of those two layers. In one example, the intermediate layer 314 is an elastomer (e.g., silicone), and the first layer 310 is a porous polymer (e.g., ePTFE).

The intermediate layer 314 has a transition portion intermediate layer wall thickness 316 that varies along the transition portion 308. The transition portion intermediate layer wall thickness 316 may taper between the transition portion proximal end 304 and the transition portion distal end 300 as shown in FIGS. 3A-B. The transition portion intermediate layer wall thickness 316 may be thinner near the transition portion proximal end 304 than the transition portion distal end 300. Alternatively, the transition portion intermediate layer wall thickness 316 may be thicker at the transition portion proximal end 304 than the transition portion distal end 300.

The intermediate layer 314 may also be juxtaposed to an optional additional layer (e.g., second layer 318). Alternatively, the intermediate layer 314 may be partially imbibed into another layer, for example, the second porous layer 318, in the surface region of the second layer 318 that is adjacent to the intermediate layer 314. The intermediate layer 314 may extend proximally and/or distally beyond the transition portion 308.

The transition portion 308 may have a second (outer) layer 318. For example, as shown in FIGS. 3A-C, the transition portion 308 has a second layer 318, adjacent to the intermediate layer 314, with a transition portion second layer wall thickness 320. The transition portion second layer wall thickness 320 may taper between the transition portion proximal end 304 and the transition portion distal end 300, as shown in FIGS. 3A-C. The transition portion intermediate layer wall thickness 316 may be thicker near the transition portion proximal end 304 than near the transition portion distal end 300. Alternatively, the transition portion proximal end 304 may be thinner than the transition portion distal end 300. The second layer 318 may extend proximally and/or distally beyond the transition portion 308.

In certain instances, the intermediate layer 314 may taper between the transition portion proximal end 304 and the transition portion distal end 300. In certain instances, the intermediate layer 314 may taper such that the intermediate layer wall thickness 316 is zero or approximately zero at any point within the transition portion length 324 (as is represented by the dotted lines showing the boundary of the intermediate layer 314). In certain instances, the intermediate layer 314 may taper such that the intermediate layer wall thickness 316 is zero or approximately zero the at the transition portion proximal end 304. As shown in FIG. 3B, the intermediate layer 314 tapers at a constant rate toward the transition portion proximal end 304. In certain instances, the taper of the intermediate layer wall thickness 316 between the transition portion proximal end 304 and the transition portion distal end 300 may be non-constant and may increase or decrease in rate as it approaches the transition portion proximal end 304. As shown in FIG. 3B, the proximal portion 322 does not include the intermediate layer 314. The lack of the intermediate layer 314 being present in the proximal portion 322 (and/or the decrease in thickness of the intermediate layer 314 in the transition portion length 324) may enhance the ease of puncture of the proximal portion 322 (or the transition portion length 324) by a suture (or the like) to secure the implantable device 100 to a patient. In certain instances, the transition portion second layer wall thickness 320 may increase in thickness toward the transition portion proximal end 304 as the intermediate layer wall thickness 316 decreases in thickness (e.g., as shown in FIG. 3B). In other instances, the transition portion first layer wall thickness 312 may increase in thickness toward the transition portion proximal end 304 as the intermediate layer wall thickness 316 decreases in thickness.

In other instances, an overall wall thickness of the implantable device 100 within the transition portion length 324 may decrease as the intermediate layer wall thickness 316 decreases.

Also as shown in FIGS. 3A-C, the implantable device 100 may have a distal portion 338 between the transition portion distal end 300 and a distal portion distal end 102. The distal portion 338 may have varying diameters (inside and/or outside) along the distal portion 338 or it may have constant diameters. For example, the distal portion 338 has a constant distal portion outer diameter 108 between the distal portion distal end 102 and the transition portion distal end 300, as shown in FIGS. 3A-C. The distal portion 338 may have a constant distal portion inside diameter 113 between the distal portion distal end 102 and the transition portion distal end 300. The distal portion 338 may comprise a first layer 310 having a distal portion first layer wall thickness 344, an intermediate layer 314 having a distal portion intermediate layer wall thickness 348, and a second layer 318 having a distal portion second layer wall thickness 352.

Also as shown in FIGS. 3A-C, the implantable device 100 may have a proximal portion 322 between a proximal portion proximal end 106 and transition portion proximal end 304. The proximal portion 322 may have varying diameters (inside and/or outside) along the proximal portion 322 or it may have constant diameters. For example, the proximal portion 322 has the same proximal portion outer diameter 110 between the proximal portion proximal end 106 and the transition portion proximal end 304, as shown in FIGS. 3A-C. The proximal portion 322 may have a proximal portion inside diameter 111 that is constant between the proximal portion proximal end 106 and the transition portion proximal end 304 or alternatively, may have a varying proximal portion inside diameter 111. The proximal portion 322 may comprise a proximal portion first layer 310 having a proximal portion first layer wall thickness 328, a proximal portion intermediate layer 314 having a proximal portion intermediate layer wall thickness 332, and a proximal portion second layer 318 having a proximal portion second layer wall thickness 336.

In certain instances, the proximal portion intermediate layer 314 may taper between the transition portion proximal end 304 and the proximal end 106. In certain instances, the intermediate layer 314 may taper such that the intermediate layer wall thickness 332 is zero or approximately zero at any point within the proximal portion length 325 (as is represented by the dotted lines showing the boundary of the intermediate layer 314). In certain instances, the intermediate layer 314 may taper such that the intermediate layer wall thickness 332 is zero or approximately zero the at the proximal end 106. The decrease in thickness of the intermediate layer 314 in the proximal portion 322 may enhance the ease of puncture of the proximal portion 322 by a suture (or the like) to secure the implantable device 100 to a patient. As shown in FIG. 3C, the intermediate layer 314 tapers at a constant rate toward the proximal end 304. In certain instances, the taper of the intermediate layer wall thickness 332 between the transition portion proximal end 304 and the proximal end 106 may be non-constant and may increase or decrease as it approaches the proximal end 106. In certain instances, the proximal portion first layer wall thickness 328 may increase in thickness toward the proximal end 106 as the proximal portion intermediate layer 314 decreases in thickness (e.g., as shown in FIG. 3C). In other instances, the proximal portion second layer wall thickness 336 may increase in thickness toward the proximal end 106 as the intermediate layer wall thickness 332 decreases in thickness.

In other instances, an overall wall thickness of the implantable device 100 within the proximal portion length 325 may decrease as the intermediate layer wall thickness 332 decreases.

The transition portion 308 has a transition portion proximal end 304 (FIG. 5) with a transition portion proximal end outer diameter 306 and a transition portion proximal end inside diameter 307. The implantable device 100 also has a transition portion distal end 300 (FIG. 4) with a transition portion distal end outer diameter 302, and a transition portion distal end inside diameter 303. The transition portion distal end diameters (302,303) may be the same diameter as distal portion distal end diameters (108,113). The transition portion proximal end diameters (306,307) may be the same diameter as proximal portion proximal end diameters (110, 111).

The proximal portion 322 may have various wall thickness configurations. In one example, as shown in FIG. 3A, the proximal portion 322 has a first layer 310, an intermediate layer 314, and a second layer 318. The first layer 310 has a proximal portion first layer wall thickness 328 that is substantially the same thickness along the proximal portion 322 and meets the transition portion first layer wall thickness 312 at the transition portion proximal end 304. The intermediate layer 314 has a proximal portion intermediate layer wall thickness 332 that is substantially the same thickness along the proximal portion 322 and meets the transition portion intermediate layer wall thickness 316 at the transition portion proximal end 304. The second layer 318 has a proximal portion second layer wall thickness 336 that is substantially the same thickness along the proximal portion 322 and meets the transition portion second layer wall thickness 320 at the transition portion proximal end 304. Alternatively, the proximal portion 322 may have wall thicknesses that are not constant along the proximal portion length 325.

The distal portion 338 may have various wall thickness configurations. In one example, as shown in FIGS. 3A-C, the distal portion 338 has a first layer 310, an intermediate layer 314, and a second layer 318. The first layer 310 has a distal portion first layer wall thickness 344 that is substantially the same thickness along the distal portion 338 and meets the transition portion first layer wall thickness 312 at the transition portion distal end 300. The intermediate layer 314 has a distal portion intermediate layer wall thickness 348 that is substantially the same thickness along the distal portion 338 and meets the transition portion intermediate layer wall thickness 316 at the transition portion distal end 300. The second layer 318 has a distal portion second layer wall thickness 352 that is substantially the same thickness along the distal portion 338 and meets the transition portion second layer wall thickness 320 at the transition portion distal end 300. Alternatively, the distal portion 338 may have wall thicknesses that are not constant along the distal portion length 326.

Figure 4:
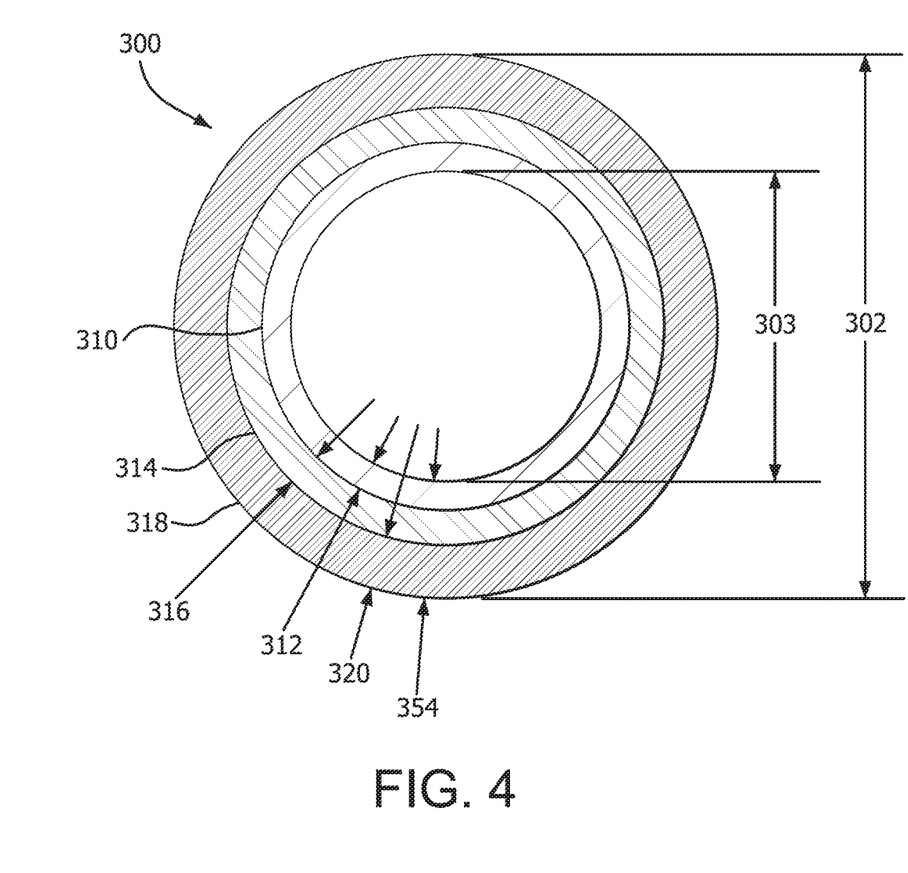
FIG. 4 shows a transverse cross section taken at a designated location on the longitudinal cross section of FIG. 3A.

The implantable device 100 may have various overall wall thickness configurations. For example, as shown in FIG. 4, the transition portion 308 (also shown in FIGS. 3A-C) may have a transition portion distal end overall wall thickness 354 at the transition portion distal end 300 that is less than a transition portion proximal end overall wall thickness 356 at the transition portion proximal end 304. The transition portion overall wall thickness at a location along the transition portion may vary between transition portion overall wall thicknesses (354,356).

An overall wall thickness measured along the implantable device 100 may comprise at least one polymer layer (e.g., ePTFE) and at least one elastomer layer (e.g., silicone). The implantable device 100 may have a transition portion 308 comprising a transition portion overall wall thickness 354 (as shown in FIG. 4). A transition portion wall thickness ratio, taken along the transition portion 308 (e.g., at transition portion distal end 300), of transition portion intermediate layer wall thickness 316 to a combination of transition portion first layer wall thickness 312 and transition portion second layer wall thickness 320 is equal to 1. In other words, this ratio is the ratio of the intermediate layer wall thickness to the combination of the inner and outer layer wall thicknesses. In other cases, the transition portion distal end wall thickness ratio may be greater than 1.0, for example, 1.1, 1.2, 1.3, 1.4, 1.5 or even greater. Still, in other cases, the transition portion wall thickness ratio may be less than 1.0, for example, 0.7, 0.8, or 0.9.

Figure 5:
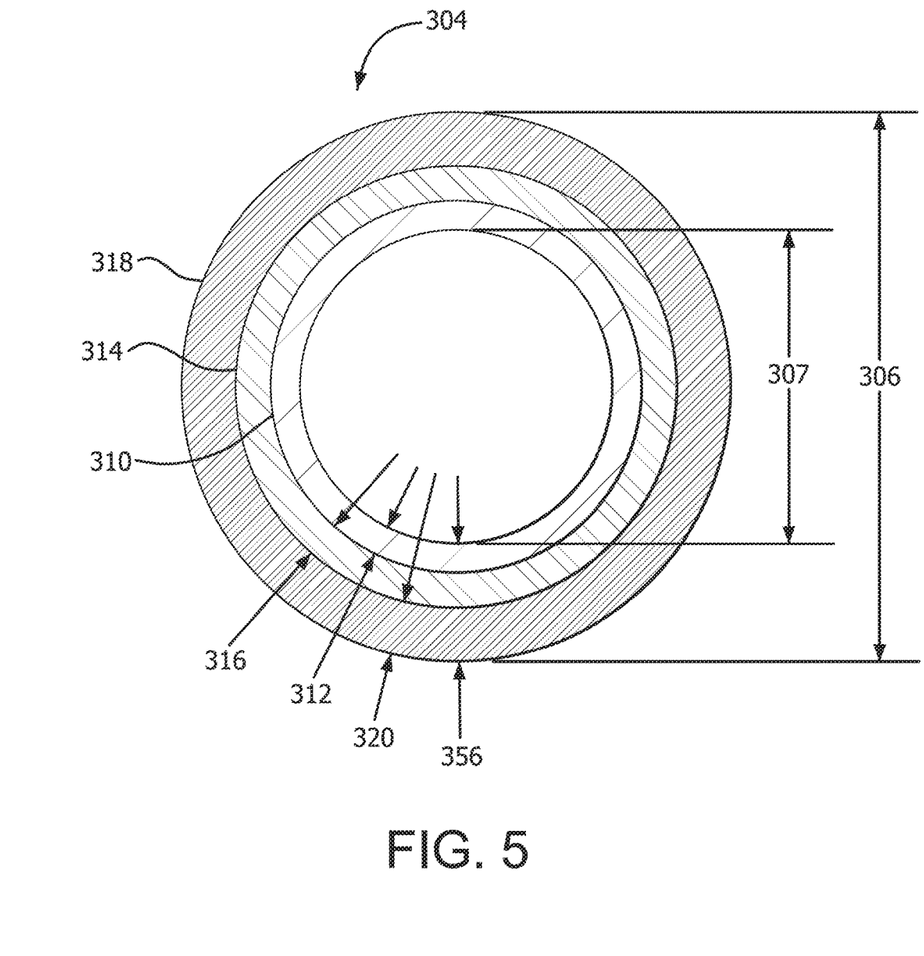
FIG. 5 shows another transverse cross section taken at a designated location on the longitudinal cross section of FIG. 3A.

The implantable device 100 may also have a transition portion 308 comprising a transition portion overall wall thickness 356 (FIG. 5). A transition portion wall thickness ratio, taken along the transition portion 308 (e.g., at transition portion proximal end 304), of the transition portion intermediate layer wall thickness 316 to a combination of the transition portion first layer wall thickness 312 and the transition portion second layer wall thickness 320 is less than 1. For example, the transition portion proximal end ratio of the transition portion intermediate layer wall thickness 316 to a combination of the transition portion first layer wall thickness 312 and the transition portion second layer wall thickness 320 may be 0.9, 0.8, 0.7, 0.6, 0.5, 0.4 or less. The transition portion proximal end ratio may extend along the implantable device 100 to a proximal portion 322, as shown in FIG. 3A. Similarly, the transition portion distal end ratio may extend along the implantable device 100 to a distal portion 338, also as shown in FIG. 3A.

In addition to the ratios described above, the overall wall thickness 356 at the transition portion proximal end 304 may be greater than the overall wall thickness 354 at the transition portion distal end 300.

The implantable device 100 may have various portions. For example, it may have a proximal portion 322 with a proximal portion length 325, a transition portion 308 with a transition portion length 324, and a distal portion 338 with a distal portion length 326, as shown in FIGS. 3A-C. The proximal portion length 325 may be shorter than the transition portion length 324 and the transition portion length 324 may be shorter than the distal portion length 326. The distal portion length 326 may be 15 cm, 20 cm, 30 cm, 40 cm, 50 cm or more, and the transition portion length 324 may be 5 cm (other lengths may range from 1 cm to 10 cm), and the proximal portion length 325 may be approximately 2 cm (other lengths may range from 1 cm to 10 cm). Other combinations of lengths are contemplated and dependent upon application. In some cases, the implantable device 100 may be entirely a transition portion 308 (i.e., the entire graft is tapered) and therefore may have a transition portion length 324 of 20 cm, 30 cm, 40 cm, or 50 cm or more.

An implantable device 100 may be manufactured in various ways. One example is described herein, as follows. A 145 cm long mandrel having a 7 mm diameter portion by 120 cm long, a 3.84 mm diameter portion by 20 cm long, and a 5 cm long tapered portion between the 7 mm diameter portion and the 3.84 mm diameter portion was obtained (i.e., a 7-4 mm tapered mandrel). A 3.60 mm diameter extruded ePTFE tube with a wall thickness of 0.08 mm was obtained (ePTFE first tube). The ePTFE first tube has a lumen extending along the ePTFE first tube. The 7-4 mm tapered mandrel was then inserted into the ePTFE first tube. The ePTFE first tube was extended so that any wrinkling of the ePTFE first tube was minimized. The ePTFE first tube was then helically wrapped with a 1.27 cm wide ePTFE film tape entirely along the length of the ePTFE first tube. The mandrel with the ePTFE first tube was then heated in a convection oven at 370 degrees C. for 12 minutes. Following removal from the oven, the ePTFE first tube on the 7-4 mm tapered mandrel was then allowed to air cool in ambient air until the ePTFE tube reached approximately room temperature. This example produced an ePTFE first tube with approximately a 7 mm inside diameter length portion, a 4 mm inside diameter length portion, and a tapered length portion extending between the 7 mm inside diameter length portion and the 4 mm inside diameter length portion. The 7 mm inside diameter length portion had a wall thickness of approximately 0.08 mm and the 4 mm inside diameter length portion had a wall thickness of approximately 0.10 mm. The tapered length portion had a varying wall thickness (i.e., varying from 0.08 mm to 0.10 mm) between the 7 mm inside diameter length portion and the 4 mm inside diameter length portion.

A second ePTFE tube with a taper was manufactured as follows. A 145 cm long mandrel with a 6.50 mm diameter portion by 110 cm long, a 3.80 mm diameter portion by 30 cm long, and a 5 cm long tapered length portion between the 6.50 mm diameter length portion and the 3.80 mm diameter length portion was obtained (6.5 -3.80 mm tapered mandrel). A 6 mm diameter extruded and expanded ePTFE tube with a wall thickness of 0.66 mm was obtained (ePTFE second tube). The 6.50-3.80 mm tapered mandrel was inserted into the ePTFE second tube lumen. The ePTFE second tube was extended so that any wrinkling of the ePTFE second tube was minimized. The ends of the ePTFE second tube were then secured to the mandrel by wrapping an ePTFE film around the ends of the ePTFE second tube. The ePTFE second tube was then helically wrapped with a 1.90 cm wide ePTFE film tape entirely along the length of the ePTFE second tube. The mandrel with the ePTFE second tube was then heated by a convection oven at 370 degrees C. for 12 minutes. Following removal from the oven, the ePTFE second tube on the mandrel was then allowed to air cool in ambient air until the ePTFE second tube and mandrel reached approximately room temperature. The ePTFE second tube was then removed from the mandrel. This procedure resulted in an ePTFE second tube with a 6.5 mm inside diameter length portion, a 3.80 mm inside diameter length portion, and a tapered length portion extending between the 6.50 mm inside diameter length portion and the 3.80 mm inside diameter length portion. The 6.50 mm inside diameter length portion had a wall thickness of approximately 0.76 mm and the 3.80 mm inside diameter length portion had a wall thickness of approximately 0.79 mm. The tapered length portion had a varying wall thickness that tapered between the wall thickness of the 6.50 mm inside diameter length portion and the wall thickness of the 3.80 mm inside diameter length portion. In certain instances, the tapered length portion had a varying wall thickness that tapered between the wall thickness of the 6 mm inside diameter length portion and the wall thickness of the 4 mm inside diameter length portion, and in other instances, the tapered length portion had a varying wall thickness that tapered between the wall thickness of the 5 mm inside diameter length portion and the wall thickness of the 4 mm inside diameter length portion.

The mandrel with the ePTFE first tube was then coated with a layer of silicone (NuSil Technology LLC, Carpinteria, Calif.). An iris apparatus (Standa Ltd., Vilnius, Lithuania)

capable of dilating and contracting between 1 mm and 15 mm was obtained. The mandrel with the first ePTFE tube was displaced through the iris contained within an apparatus. The apparatus supplied silicone to the outer surface of the ePTFE first tube and the iris maintained a wall thickness of silicone of approximately 0.53 mm on the ePTFE first tube outer surface (along the larger diameter portion of the ePTFE first tube), 0.30 mm on the smaller diameter portion of the ePTFE first tube, and a varying silicone wall thickness between 0.53 mm and 0.30 mm along the tapered portion of the ePTFE first tube. The silicone was then allowed to partially set by curing in a convection oven for 6.5 minutes at 200 degrees C.

The ePTFE second tube was then enlarged diametrically by pulling the ePTFE second tube over a mandrel. The mandrel had a 9.60 mm outside diameter length portion of approximately 55 cm length and a 5.40 mm outside diameter length portion of 12 cm length with a transition length portion extending between the 5.40 mm outside diameter length portion and the 9.60 mm outside diameter length portion. The ePTFE second tube and mandrel assembly was then heated in a convection oven for approximately 45 seconds at 200 degrees C. The ePTFE second tube distal end inside diameter was enlarged to approximately 9.60 mm over the ePTFE second tube distal end and the ePTFE second tube proximal end inside diameter was enlarged to approximately 5.40 mm on the ePTFE second tube proximal end with the transition length portion extending between the 9.60 mm inside diameter and the 5.40 mm inside diameter.

After the ePTFE second tube was removed from the mandrel, a flare of 12 mm was then created on the ePTFE second tube distal end (i.e., 9.60 mm inside diameter end) with a flaring tool (a mandrel). The ePTFE second tube was then held within the apparatus with the iris to allow the ePTFE first tube with its outer layer of silicone to be inserted into the lumen of the ePTFE second tube. The ePTFE first tube proximal portion was inserted first through the ePTFE second tube distal portion until the transition length portions of the ePTFE first tube and ePTFE second tube were approximately aligned. While the ePTFE first tube was being inserted through the ePTFE second tube the apparatus applied a second layer of silicone approximately 0.15 mm thick (the second layer being thinner than the first layer) onto the ePTFE first tube with silicone outer layer. The second layer of silicone wall thickness was controlled by the iris apparatus. After the second layer of silicone was applied and the ePTFE first tube and ePTFE second tube tapered portions were aligned, the silicone was then allowed to fully set by curing in a convection oven for 15 minutes at 200 degrees C. In this example, an implantable device according to this disclosure was made.

The resulting implantable device had a first layer comprising an ePTFE first (Inner) tube, an intermediate layer comprising silicone, and a second layer comprising an ePTFE second (outer) tube. The implantable device had a transition length portion with a length of 5 cm, a distal length portion with a length of 48 cm and a proximal length portion with a length of 2 cm. Longitudinal cross sections were taken and wall thickness measurements were made (overall wall thickness and intermediate layer wall thickness) with an optical profiler (Unitron Inc., Bohemia N.Y.) along the proximal length portion and the distal length portion of the implantable device. The overall wall thickness in the proximal length portion was approximately 1.25 mm. The intermediate layer wall thickness in the proximal length portion was approximately 0.48 mm. The overall wall thickness in the distal length portion was approximately 1.22 mm and the intermediate layer wall thickness in the distal length portion was 0.70 mm. The overall wall thickness in the transition length portion varied from 1.25 mm near the proximal length portion to 1.22 mm near the distal length portion and the intermediate layer wall thickness in the transition length portion varied from 0.48 mm near the proximal length portion to 0.70 mm near the distal length portion. A ratio of intermediate layer wall thickness to a combination of the ePTFE first tube wall thickness and ePTFE second tube wall thickness in the proximal length portion was approximately 0.63. A ratio of intermediate layer wall thickness to a combination of the ePTFE first tube wall thickness and ePTFE second tube wall thickness in the distal length portion was approximately 1.35 mm.

Implantable devices according to this disclosure may be used in various applications. For example, the implantable device may be used in an arterial venous application such as in dialysis. One end of the implantable device may be attached to a vein, an opposing end may be attached to an artery.

In addition to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:
1. An implantable device comprising:
a tubular structure having a proximal end portion and a distal end portion with a distal end portion, a transition portion having a transition portion proximal end with a transition portion proximal end inside diameter, a transition portion distal end with a transition portion distal end inside diameter that is greater than the transition portion proximal end inside diameter, and a transition portion length between the transition portion proximal end and the transition portion distal end;
wherein the tubular structure has a first layer comprising a porous polymer, a second layer, and at least one intermediate layer adjacent the first layer; and
wherein the intermediate layer has a variable wall thickness extending at least partially along the transition portion length and wherein an intermediate layer wall thickness is greater within the distal end portion than the intermediate layer wall thickness within the proximal end portion.

2. The implantable device of claim 1 wherein the intermediate layer comprises an elastomer.

3. The implantable device of claim 1 wherein the tubular structure further comprises a proximal portion, and a distal portion.

4. The implantable device of claim 1 wherein the first layer is ePTFE.

5. The implantable device of claim 1 wherein the intermediate layer has an intermediate layer wall thickness at the transition portion distal end that is greater than an intermediate layer wall thickness at the transition portion proximal end.

6. The implantable device of claim 2 wherein the intermediate layer is silicone.

7. The implantable device of claim 3 wherein the distal portion has a length between the transition portion distal end and a distal portion distal end that is greater than the transition portion length and the transition portion length is greater than a proximal portion length between a proximal portion proximal end and the transition portion proximal end.

8. The implantable device of claim 1 wherein the second layer is ePTFE.

9. The implantable device of claim 1 wherein the intermediate layer wall thickness tapers from the transition portion distal end to the transition portion proximal end, and the intermediate layer wall thickness of the intermediate layer at the transition portion proximal end is zero.

10. An implantable device comprising:
a tubular structure having a first layer, an intermediate layer comprising an elastomer, a second layer, and a length between a proximal end and a distal end;
wherein said proximal end has a proximal inside diameter, and said distal end has a distal inside diameter, wherein the proximal inside diameter is less than the distal inside diameter and there is a transition portion length located between the proximal inside diameter and the distal inside diameter;
wherein the first layer and second layer comprise a porous material; and
wherein the intermediate layer has an intermediate layer wall thickness along the length of the tubular structure, wherein the intermediate layer wall thickness is greater at the distal end than it is at the proximal end.

11. The implantable device of claim 10 wherein the intermediate layer comprises silicone.

12. The implantable device of claim 10 wherein the first layer comprises ePTFE.

13. The implantable device of claim 10 wherein the second layer comprises ePTFE.

14. The implantable device of claim 10 wherein the first layer and second layer comprise ePTFE.

15. The implantable device of claim 10 wherein the first layer has a first layer wall thickness that is greater at the proximal end than at the distal end and the second layer has a second layer wall thickness that is greater at the proximal end than at the distal end.

16. The implantable device of claim 15 further comprising an overall wall thickness wherein the overall wall thickness is greater at the proximal end than at the distal end.

17. The implantable device of claim 10 further comprising a ratio of the intermediate layer wall thickness to a combination of the first layer wall thickness and the second layer wall thickness, wherein the ratio is greater than 1 at the proximal end.

18. The implantable device of claim 10 further comprising a ratio of the intermediate layer wall thickness to a combination of the first layer wall thickness and the second layer wall thickness, wherein the ratio is less than 1 at the distal end.

19. The implantable device of claim 10 wherein the intermediate layer wall thickness at the proximal end is zero.

20. An implantable device comprising:
a tubular structure having a first layer, an intermediate layer comprising an elastomer, a second layer, a proximal end portion and a distal end portion with a distal end portion diameter being greater than a proximal end portion diameter, and a length between a proximal end and a distal end;
wherein said proximal end has a proximal inside diameter, and said distal end has a distal inside diameter, wherein the proximal inside diameter is less than the distal inside diameter and there is a transition portion length located between the proximal inside diameter and the distal inside diameter;
wherein the first layer and second layer comprise a porous material; and
wherein the intermediate layer has an intermediate layer wall thickness along the length of the tubular structure, wherein the intermediate layer wall thickness decreases in thickness as one of the first layer and the second layer increases in thickness and wherein the intermediate layer wall thickness is greater within the distal end portion than the intermediate layer wall thickness within the proximal end portion.

* * * * *